(12) United States Patent
Kirsch

(10) Patent No.: US 10,214,739 B2
(45) Date of Patent: Feb. 26, 2019

(54) RNA BINDING SOLUTION

(71) Applicant: AXAGARIUS GmbH & Co. KG, Duren (DE)

(72) Inventor: Christoph Kirsch, Pulheim (DE)

(73) Assignee: AXAGARIUS GMBH & CO. KG, Duren (DE)

( * ) Notice: Subject to any disclaimer, the term of this patent is extended or adjusted under 35 U.S.C. 154(b) by 88 days.

(21) Appl. No.: 14/928,978

(22) Filed: Oct. 30, 2015

(65) Prior Publication Data

US 2017/0121702 A1    May 4, 2017

(51) Int. Cl.
| | |
|---|---|
| *G01N 1/34* | (2006.01) |
| *C12Q 1/68* | (2018.01) |
| *C12N 15/10* | (2006.01) |
| *C07H 21/02* | (2006.01) |
| *C07H 1/06* | (2006.01) |
| *C07H 1/08* | (2006.01) |

(52) U.S. Cl.
CPC .............. *C12N 15/101* (2013.01); *C07H 1/06* (2013.01); *C07H 1/08* (2013.01); *C07H 21/02* (2013.01); *C12N 15/1006* (2013.01)

(58) Field of Classification Search
CPC .............. G01N 1/34; C12Q 1/68; C07H 21/00
See application file for complete search history.

(56) References Cited

U.S. PATENT DOCUMENTS

| | | | | |
|---|---|---|---|---|
| 6,180,778 B1 * | 1/2001 | Bastian | ............... | C12N 15/1006 536/25.3 |
| 7,282,470 B2 * | 10/2007 | Tucker | ............... | A61K 31/19 252/186.38 |
| 2001/0021518 A1 * | 9/2001 | Goudsmit | ............... | C12N 15/10 435/91.2 |
| 2005/0059024 A1 * | 3/2005 | Conrad | ............... | C12N 15/1003 435/6.12 |
| 2005/0074753 A1 * | 4/2005 | Goldsborough | ....... | C07H 21/00 435/5 |
| 2007/0099192 A1 * | 5/2007 | Wang | ................... | C12Q 1/6837 435/6.14 |
| 2007/0249821 A1 * | 10/2007 | Bitner | ................... | C07H 21/00 536/25.4 |
| 2012/0252693 A1 * | 10/2012 | Umansky | ............. | C12Q 1/6883 506/9 |
| 2012/0272968 A1 * | 11/2012 | Kirschner | ........... | A01M 31/008 128/206.13 |
| 2013/0041145 A1 * | 2/2013 | Kirsch | ..................... | C12N 1/06 536/25.41 |

OTHER PUBLICATIONS

Ahern, H., The Scientist 9 (15) : 20 (1995).*
Mico Bio-Spin Columns : Product Information BioRad Laboratories Downloaded from Internet on May 2017.*
Stratagene Catalog p. 39 (1988).*
Machine Translation of JP2006271292.*
Wikipedia; "Spin column-based nucleic acid purification", 2 pages. https://en.wikipedia.org/wiki/Spin_column-based_nucleic_acid_purification?oldid=781708703.

\* cited by examiner

*Primary Examiner* — Ethan C Whisenant
(74) *Attorney, Agent, or Firm* — International IP Law Group, PLLC

(57) ABSTRACT

The subject innovation relates to a RNA binding buffer comprising (a) at least one chaotropic agent; and (b) an organic solvent selected from the group consisting of ethylene carbonate, ethylene glycol diacetate and 2-pyrrolidone or combinations thereof. The subject innovation further relates to a method of binding RNA to a solid support and to a method of isolating RNA both making use of the binding buffer of the subject innovation. The subject innovation finally relates to a kit comprising the RNA binding buffer or the organic solvent as relevant substance therein.

26 Claims, 2 Drawing Sheets

1

RNA BINDING SOLUTION

BACKGROUND

Many biological techniques, including gene expression analyses such as hybridization assays, reverse transcription polymerase chain reaction (RT-PCR), cloning, restriction analysis, and sequencing use high-purity, intact RNA.

Several methods for isolating RNA are known which fall into two general categories, namely liquid phase and solid phase purification. In liquid phase isolation, the RNA remains in the liquid phase while impurities are removed by processes such as precipitation and/or centrifugation. In solid phase isolation, the RNA is bound to a solid support while impurities such as DNA, proteins and phospholipids are selectively eluted or do not bind at all to said solid support.

A widespread method of RNA isolation involves the use of chaotropic agents and organic solvents in order to bind the RNA to a solid phase, such as silica. Hereby, several organic solvents have been identified as suitable for this purpose such as alcohols (e.g. methanol, ethanol or isopropanol; see EP1 502 951 A1), ketones (e.g. diethylketone, methylethylketone, methylpropylketone, isobutylmethylketone; see EP 1 524 317 A1) or ethers such as diethylene glycole diethylether (see EP 1 529 841 A1). Most of the compounds are critical with regard to inflammability or toxicity or at least exhibit a very unpleasant odor. Furthermore, the RNA yields and the RNA integrity are often suboptimal and the DNA contamination is always a critical issue.

Hence, there is still a need for an improved methods and reagents for isolation of RNA.

SUMMARY

In a first aspect, the subject innovation provides a phenol-free RNA binding buffer that allows RNA to bind selectively to an RNA-binding solid phase and that includes a chaotropic agent and an organic solvent selected from the group consisting of ethylene carbonate, ethylene glycol diacetate and 2-pyrrolidone, or combinations thereof.

The subject innovation is based on the surprising finding that the RNA yield can be significantly increased and the DNA contamination can be reduced if at least one of the organic solvents of the subject innovation and at least one chaotropic agent are included in the RNA binding buffer that is used for binding the RNA to a solid phase. It was found that including at least one chaotropic agent and at least one of the listed organic solvents in the RNA binding buffer has the advantage that the quality of the RNA is excellent, even if rather critical biological samples are used. The subject innovation further is based on the finding that the moderate solubility of the claimed organic solvents in water is substantially increased by the addition of the chaotropic agent to the buffer.

The binding solution of the subject innovation has several advantages over RNA binding solutions known.

The three organic solvents, namely ethylene glycol diacetate, 2-pyrrolidone, and ethylene carbonate, all represent substances with a high flash point and a high ignition temperature, and are therefore associated with a lower risk of inflammation than methanol, ethanol, acetone and other organic solvents described in the background.

Furthermore, these substances are of lower toxicity than many other known organic solvents, which represents an advantage with regard to user compliance.

The rather low costs for these organic solvents represent a further advantage.

The binding solution of the subject innovation can be used for a broad spectrum of biological samples including bacteria, eukaryotic cells, tissues, organs, bones, and plant tissue.

Additionally, for many types of biological samples, the binding solution including said organic solvents results in an increased yield of RNA compared to the classical binding solutions including ethanol.

Furthermore, the RNA as isolated with the binding buffer of the subject innovation, is of high integrity, which in many cases, has an RNA integrity number (RIN) above 9.0.

A further advantage is that the DNA contamination can be substantially reduced when using the binding buffer of the subject innovation.

The binding buffer can be used in combination with the well-known chaotropic agents and also with well-known solid supports. Hence, the isolation methods of known techniques can be easily adjusted to the method of the subject innovation.

Accordingly, a kit including said binding buffer (or one of its constituents, such as, the organic solvent) can be easily produced in a cost-efficient manner.

It shall be understood that one embodiment of the subject innovation can also be any combination of the dependent claims with the respective independent claim. Further advantageous embodiments are defined below.

The subject innovation relates to a RNA binding buffer, to a method of binding RNA to a solid support, and to a method of isolating RNA, both methods making use of the binding buffer of the subject innovation. The subject innovation further relates to a kit including the binding buffer or the organic solvent as relevant substance therein.

According to the subject innovation, the RNA-binding buffer is a phenol-free binding buffer. In the context of the subject innovation, the term, "phenol-free," is defined as the absence of phenol in the buffer solution so that the lysis buffers according e.g. the method of Comczyinski and Sacchi (Anal. Biochem, 1987, 162: 156-159) do not represent a binding buffer according to the subject innovation. Furthermore, binding buffers which represent the aqueous phase in the phenolic phase separation methods, and which therefore contain only traces of phenol, do not constitute a phenol-free buffer according to the subject innovation.

In one embodiment, the RNA-binding buffer is an aqueous buffer, in the sense that the claimed three organic solvents are the only organic solvents in the buffer, and are complemented by water as the second type of solvent.

The binding buffer further includes an organic solvent selected from the group consisting of ethylene carbonate, ethylene glycol diacetate and 2-pyrrolidone or combinations thereof. Hence, the following seven general compositions for the binding solution shown in Table 1, are subject of the subject innovations:

TABLE 1

| # | Binding buffer includes the following organics solvents: | | |
|---|---|---|---|
| 1 | EDGA | — | — |
| 2 | 2-Pyrrolidone | — | — |
| 3 | Ethylcarbonate | — | — |
| 4 | EDGA | 2-Pyrrolidone | — |
| 5 | EDGA | Ethylcarbonate | — |

TABLE 1-continued

| # | Binding buffer includes the following organics solvents: | | |
|---|---|---|---|
| 6 | Ethylcarbonate | 2-Pyrrolidone | — |
| 7 | Ethylcarbonate | 2-Pyrrolidone | EDGA |

According to the subject innovation, the RNA binding solution includes at least one chaotropic agent. The addition of the chaotropic agent denatures RNAses and preserves the quality of the RNA contained in the solution after lysis of the cells.

Any chaotropic agent can be used for the RNA binding solution of the subject innovation that causes disorder in a protein or nucleic acid by, for example, but not limited to, altering the secondary, tertiary or quaternary structure of a protein or a nucleic acid, while leaving the primary structure intact. A chaotropic salt may be used. Chaotropic agents include, but are not limited to, chaotropic salts including e.g. thiocyanate, isothiocyanate, perchlorate, trichloroacetate, trifluoroacetate or iodide and/or including guanidinium and are selected from guanidinium hydrochloride (GHCl), guanidinium thiocyanate, guanidinium isothiocyanate (GITC), sodium thiocyanate, sodium iodide, sodium perchlorate, sodium trichloroacetate, sodium trifluroacetate, urea and the like.

In one embodiment, the chaotropic agent is GHCl or GITC, or an equally strong chaotropic agent. Respective strong chaotropic agents are very efficient in protecting the nucleic acid, in particular RNA, from degradation.

According to one embodiment, the RNA binding buffer (and possibly also the preceding lysis solution) includes the chaotropic agent in a concentration selected from the group consisting of 0.25 M up to the saturation limit, 0.5 to 3M, 0.75 M to 2 M, and at least 1M. As is shown in the examples, using a respective concentration is useful to efficiently preserve the integrity of the incorporated RNA.

According to the subject innovation, the volume of the organic solvent, which is added to one volume of lysate containing lysed sample material, RNA, and chaotropic agent, is between 10% v/v and 50% v/v, preferably between 15% v/v and 40% v/v, and more preferably between 20% v/v and 30% v/v resulting in a final concentration of 10-50%, and more preferably 15-35% and more preferably 18-25%. It is noted that the optimal percentage depends on the specific organic solvent or combination of said organic solvents, and on the kind and concentration of the chaotropic agent, respectively.

In one embodiment of the subject innovation the phenol-free RNA buffer has a pH value of between 5.0 and 9.0; preferably of between 6.0 and 8.0 and more preferably of between 6.5 and 7.5.

In a second aspect, the subject innovation provides a method for binding RNA selectively to an RNA-binding solid phase, which includes contacting an RNA-binding solid phase with an RNA-containing material provided in the phenol-free RNA binding buffer according to the subject innovation.

According to the subject innovation, the RNA-binding solid phase is selected from the group consisting of silica, silica particles, silicon dioxide, diatomaceous earth, glass, alkylsilica, aluminum silicate, and borosilicate; nitrocellulose; diazotized paper; hydroxyl apatite; nylon; metal oxides; zirconia; alumina; polymeric supports, diethylaminoethyl- and triethylaminoethyl-derivatized supports, hydrophobic chromatography resins (such as phenyl- or octyl Sepharose) and may be silica.

According to one embodiment, a solid phase including silica is used. Silica based nucleic acid isolation methods are broadly used in known techniques. The solid phase including silica may e.g. have the form of a filter, fibres, membrane, silica-filled columns or particles. In one embodiment, silica fibers can be used in form of silica spin columns.

In a third aspect, the subject innovation provides a method for isolating purified RNA from a biological sample including the steps of:
(a) Generating a RNA-containing solution by lysing the biological sample with a phenol-free lysis solution including a chaotropic reagent, and optionally, enhancing the lysis by mechanical, freeze-thawing-associated or enzymatic (pre-)treatment of the biological sample;
(b) Adding a solution including ethylene carbonate, ethylene glycol diacetate or 2-pyrrolidone or combinations thereof to yield a RNA binding solution according to the subject innovation;
(c) Contacting an RNA-binding solid phase with the RNA binding solution of step (b) in order to bind the RNA to said RNA-binding solid phase;
(d) Optionally performing a DNase digest and/or proteolytic digest;
(e) Optionally performing at least one washing step for washing the RNA bound to said RNA-binding solid phase;
(f) Optionally eluting the RNA.

According to one embodiment, a protein digest is performed in step (d) which is performed by a proteolytic enzyme which is added in step (d) and thus is included in the resuspended sample.

A proteolytic enzyme refers to an enzyme that catalyzes the cleavage of peptide bounds, for example in proteins, polypeptides, oligopeptides and peptides. Exemplary proteolytic enzymes include, but are not limited to, proteinases and proteases, in particular subtilisins, subtilases, alkaline serine proteases and the like. Subtilases are a family of serine proteases, i.e. enzymes with a serine residue in the active side. Subtilisins are bacterial serine protease that has broad substrate specificities. Subtilisins are relatively resistant to denaturation by chaotropic agents, such as urea and guanidine hydrochloride and anionic detergents such as sodium dodecyl sulfate (SDS). Exemplary subtilisins include, but are not limited to, proteinase K, proteinase R, proteinase T, subtilisin, subtilisin A, and the like. In one embodiment, the proteolytic enzyme is proteinase K.

In a further embodiment the phenol-free lysis solution further includes at least one detergent and at least one chelating agent.

By using a detergent, the sample can be stabilized and/or higher yields/better RNA purity can be obtained. The detergent supports the lysis the cells contained in the sample and can further reduce protein absorption to the solid phase leading to higher RNA yield and higher purity. An anionic detergent can support the binding of DNA to a first solid support; whereas other can help to avoid binding of RNA to a first solid support in the absence of a binding solution, in order to reduce DNA contamination (see e.g. EP0743950B1).

According to one embodiment, the lysis solution includes at least one chelating agent. This chelating agent is added in a concentration so that the resuspended sample includes the chelating agent in a concentration of at least 0.5 mM, at least 2.5 mM, preferably at least 3.5 mM, more preferred at least 5 mM, at least 7.5 mM or at least 10 mM. In one embodiment, the chelating agent is added in a concentration so that the resuspended sample includes the chelating agent in a concentration selected from 0.5 mM to 100 mM, 2.5 mM to 75 mM, 2.5 mM to 60 mM, 3.5 mM to 50 mM, 3.5 mM to 30 mM, 3.5 mM to 25 mM, 3.5 mM to 20 mM, 5 mM to 15 mM and 5 mM to 10 mM.

The chelating agent that is used according to the subject innovation prevents or reduces the formation of a precipitate and/or the adherence of precipitate to the container when included in the resuspended sample. According to one embodiment, the chelating agent is an organic ligand, which is capable of forming two or more separate coordinate bonds to a metal cation and includes at least one nitrogen atom as nucleophilic coordinating atom.

According to one embodiment, the chelating agent is an organic ligand, which is capable of forming two or more separate coordinate bonds to a metal cation and includes at least four nucleophilic coordinating atoms. According to one embodiment, the chelating agent is an organic ligand, which is capable of forming two or more separate coordinate bonds to a metal cation and includes at least four carboxylic groups. According to one embodiment, the chelating agent is an organic ligand, which is capable of forming two or more separate coordinate bonds to a metal cation, the stability constant of the resulting complex being at least $10^4$ $M^{-1}$ in case of calcium as metal cation. Chelating agents according to the subject innovation include, but are not limited to, diethylene triamine pentaacetic acid (DTPA), ethylenedinitrilo-tetraacetic acid (EDTA), ethylene glycol tetraacetic acid (EGTA) and N, Nbis(carboxymethyl)glycine (NTA). According to one embodiment, EDTA is used. As used herein, the term "EDTA" indicates inter alia the EDTA portion of an EDTA compound such as, for example, $K_2EDTA$, $K_3EDTA$ or $Na_2EDTA$.

In one embodiment of the subject innovation, the method for isolating purified RNA from a biological sample includes a further DNA-removing step which is performed between step (a) and step (b) and whereby the sample is contacted with a DNA-binding solid support, which may be a silica material or a silica containing spin column.

In a further embodiment of the subject innovation, the organic solvent containing solution in step (b) of the RNA isolation method is added to the RNA-containing solution of step (a) in a volume ratio of between 1:2 and 1:5, preferably of between 1:3 and 1:4, and more preferably of 1:3.5. This has the advantage that the final volume is reduced compared to the regular addition of 70% ethanol in a ratio of 1:1. Furthermore, this reduces the quantities of the organic solvent to be used for the isolation method of the subject innovation.

In a specific embodiment of the subject innovation, the RNA purification method is performed by the following steps:

(a) A RNA containing sample (e.g. cells, tissue, or RNA containing material, up to approximately 30 mg) is contacted with a lysis buffer (350 μL, e.g. 3 M guanidinium thiocyanate, GITC) and dissolved (lysed) in this buffer;

(b) Optionally, the lysate is passed over a silica containing spin column, to which cell and tissue debris or other non-lysed material and DNA binds, to obtain a cleared lysate;

(c) A Binding Solution (100 μL ethylene glycol diacetate, ethyl carbonate or 2-pyrroidone) is added to the lysate and mixed.

(d) The mixture is passed over a silica containing spin column, to which RNA binds;

(e) The spin column is washed with a chaotropic washing solution;

(f) The spin column is washed with an alcoholic washing solution such as 80% ethanol in water;

(g) Water or low salt buffer such as TE buffer is added to the spin column and RNA is eluted.

In a fourth aspect the subject innovation provides a kit including:

(a) a phenol-free lysis solution;

(b) a solution including ethylene carbonate, ethylene glycol diacetate or 2-pyrrolidone or a combination thereof.

It is beneficial to provide the lysis solution and the claimed organic solvents as separate solutions, which then exhibit long-term stability. The reagents are then mixed during the RNA isolation to yield the final RNA binding buffer.

In one embodiment of the subject innovation, the kit further includes one or more of the following:

(a) one or more wash buffers;
(b) a DNAse containing solution;
(c) silica spin columns for DNA binding;
(d) silica spin columns for RNA binding;
(e) Tris-EDTA buffer or RNase-free $H_2O$ as elution buffer.

BRIEF DESCRIPTION OF THE DRAWINGS

These and other aspects of the subject innovation will be apparent from and elucidated with reference to the embodiments described hereinafter.

The subject innovation will now be described, by way of example, based on embodiments with reference to the accompanying drawings.

DETAILED DESCRIPTION

Figure 1:
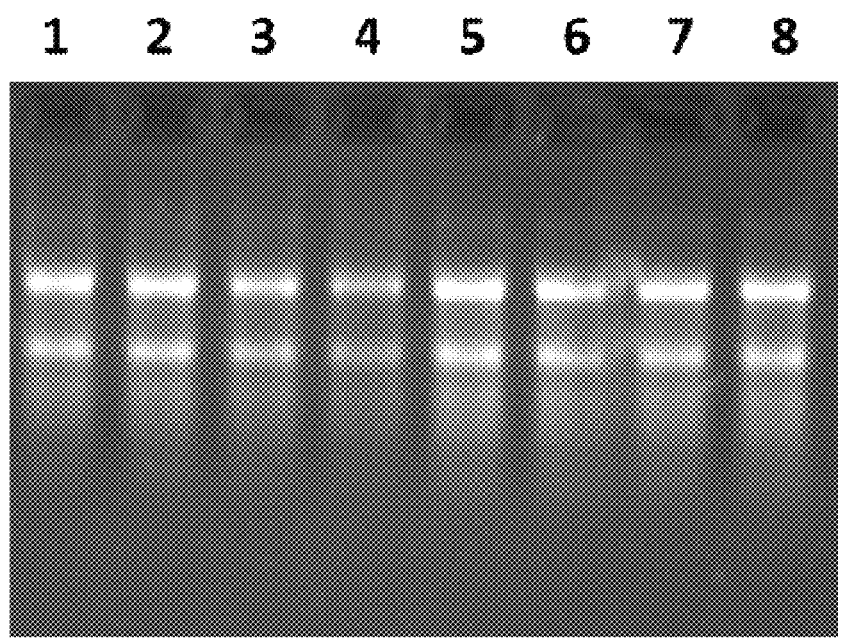
FIG. 1 shows a gel image of a denaturing gel analysis of the RNA samples as purified according to Example 4.

While the subject innovation has been illustrated and described in detail in the drawings and the foregoing description, such illustration and description are to be considered illustrative or exemplary and not restrictive.

From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "including" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

EXAMPLES

A number of $10^6$ HeLa cells were contacted and lysed with 350 μL of 5 M guanidinium thiocyanate (GITC) solution. The lysate was passed over a silica fibre-containing spin column (NucleoSpin Protein Removal Column) in order to obtain a cleared lysate. The flow-through was mixed with 350 μL of one of the following solutions 1, 4, 5, 6, 8, 10, 12, 13, 14, 15, 16, 17. The mixtures 2, 3, 7, 9, 11 were not used because they did not form a homogeneous solution. Thereafter, the samples were processed as follows: the lysate-binding solution mixtures were passed over a silica containing spin column (NucleoSpin RNA column) by centrifugation, 350 μL Membrane Desalting Buffer MDB was added and centrifuged, 95 μL of DNase containing reaction mix was added and incubated for 15 minutes, addition of 200 μL wash buffer RA2, centrifugation, addition of 600 μL wash buffer RA3, centrifugation, addition of 250 μL wash buffer RA3, centrifugation, addition of 100 water and elution of the RNA by centrifugation. NucleoSpin RNA columns, Buffers MDB, RA2, and RA3 are parts of NucleoSpin RNA kits.

The different experimental approaches together with the quantity and quality of the purified RNA are summarized in Table 2:

TABLE 2

| # | Binding Solution Substance A (% vol.) | Substance B (% vol) | Observation | RNA yield relative to reference (70% ethanolic solution) | RIN |
|---|---|---|---|---|---|
| 1 | Ethylene glycol diacetate 100% | — | Clear solution | 27% | n.d. |
| 2 | Ethylene glycol diacetate 75% | water 25% | Two phases | n.d. | n.d. |
| 3 | Ethylene glycol diacetate 50% | water 50% | Two phases | n.d. | n.d. |
| 4 | Ethylene glycol diacetate 50% | 5M GITC 50% | Clear solution | 65% | n.d. |
| 5 | Ethylene glycol diacetate 75% | 5M GITC 25% | Clear solution | 55% | n.d. |
| 6 | Pyrrolidon 100% | — | Clear solution | 14% | n.d. |
| 7 | Pyrrolidon 75% | water 25% | Tends to solidification | n.d. | n.d. |
| 8 | Pyrrolidon 50% | water 50% | Clear solution | 7% | n.d. |
| 9 | Ethylene carbonate 100% | — | Tends to solidification | n.d. | n.d. |
| 10 | Ethylene carbonate 75% | water 25% | Clear solution | 208% | 9.2 |
| 11 | Ethylene carbonate 50% | water 50% | Tends to solidification | n.d. | n.d. |
| 12 | Ethylene carbonate 50% | Pyrrolidon 50% | Clear solution | 186% | 8.5 |
| 13 | Ethylene carbonate 50% | Ethyleneglykol diacetate 50% | Clear solution | 107% | 8.1 |
| 14 | Pyrrolidon 50% | Ethylene glykol diacetate 50% | Clear solution | 137% | 9.0 |
| 15 | Pyrrolidon 75% | 5M GITC 25% | Clear solution | 26% | n.d |
| 16 | Ethylencarbonat 75% | 5M GITC 25% | Clear solution | 113% | 8.5 |
| 17 | Ethanol 70% | Water 30% | Reference | 100% (5.9 μg) | 8.4 |

RNA yield was determined spectrophotometrically, RNA Integrity Number (RIN) was determined with the Bioanalyzer (Agilent). Note that higher RIN values (RNA integrity number) values indicate a higher degree of RNA integrity. RIN values range between 10 (intact RNA) and 1 (totally degraded RNA).

RNA yield in the control preparation (Binding Solution #17) was 5.9 μg.

As obvious from the table, ethylene glycol diacetate, 2-pyrrolidone and ethylene carbonate alone, mixed among themselves, with water or with 5 M GITC solution can serve as alternative organic solvent to adjust binding conditions in a chaotropic sample lysate in order to bind RNA to and elute RNA from a silica matrix.

Example 2

RNA was isolated from $10^6$ HeLa cells according to example 1, however, as binding solution, the following mixtures were used, shown in Table 3:

TABLE 3

| Binding solution (relative volume of substances used to create the binding solution) | | RNA yield relative to | |
|---|---|---|---|
| Ethylene carbonate | Water | reference binding solution (70% ethanol) | RIN |
| 84% | 16% | 98% | 8.8 |
| 75% | 25% | 103% | 5.2 |

TABLE 3-continued

| Binding solution (relative volume of substances used to create the binding solution) | | RNA yield relative to | |
|---|---|---|---|
| Ethylene carbonate | Water | reference binding solution (70% ethanol) | RIN |
| 66% | 34% | 103% | 8.8 |
| 50% | 50% | 35% | 9.0 |

The reference preparation with 70% ethanolic solution yielded 12.8 μg RNA with a RIN of 8.9.

TABLE 4

| Binding solution (relative volume of substances used to create the binding solution) | | RNA yield relative to reference binding solution (70% ethanol) |
|---|---|---|
| Ethylene carbonate | 2-Pyrrolidone | |
| 84% | 16% | 119% |
| 75% | 25% | 120% |
| 50% | 50% | 110% |
| 25% | 75% | 106% |

The reference preparation with 70% ethanolic solution yielded 11.2 µg RNA.

TABLE 5

| Binding solution (relative volume of substances used to create the binding solution) | | RNA yield relative to reference binding solution (70% ethanol) |
|---|---|---|
| 2-Pyrrolidone | Ethylene glycol diacetate | |
| 84% | 16% | 79% |
| 75% | 25% | 82% |
| 50% | 50% | 86% |
| 25% | 75% | 90% |

The reference preparation with 70% ethanolic solution yielded 14.3 µg RNA.

As obvious from the tables, ethylene carbonate water mixtures and mixtures of 2-pyrrolidone with ethylene carbonate or ethylene glycol diacetate can serve as alternative organic solvent to adjust binding conditions in a chaotropic sample lysate in order to bind RNA to and elute RNA from a silica matrix.

Example 3

RNA was isolated from garden cress (100 mg per prep) and mouse kidney (12 mg per prep) according to example 1, however, as binding solution ethylene glycol diacetate (EGDA) was used as 25-55% solutions or emulsions in water as binding solution. RNA yields were determined spectrophotometrically.

The different experimental approaches together with the quantity of the purified RNA are summarized in Tables 6 and 7:

TABLE 6

| | Garden cress | | | | |
|---|---|---|---|---|---|
| prep # | EGDA 25% | EGDA 35% | EGDA 45% | EGDA 55% | Reference: 70% ethanol |
| 1 | 6.5 | 9.8 | 7.2 | 2.4 | 3.4 |
| 2 | 4.3 | 9.5 | 7.0 | 2.6 | 3.9 |
| 3 | 5.3 | 10.3 | 16.8 | 4.0 | 4.1 |
| 4 | 6.4 | 8.6 | 14.1 | 4.0 | 6.8 |
| average RNA yield [µg] | 5.7 | 9.6 | 11.3 | 3.2 | 4.6 |

TABLE 7

| | Mouse kidney | | | | |
|---|---|---|---|---|---|
| prep # | EGDA 25% | EGDA 35% | EGDA 45% | EGDA 55% | Reference: 70% ethanol |
| 1 | 2.9 | 7.9 | 9.5 | 2.9 | 16.1 |
| 2 | 3.0 | 10.2 | 10.9 | 7.4 | 16.8 |
| 3 | 4.2 | 9.1 | 17.2 | 7.1 | 19.4 |
| 4 | 3.8 | 10.5 | 17.9 | 5.5 | 20.9 |
| average RNA yield [µg] | 3.5 | 9.4 | 13.9 | 5.8 | 18.3 |

As obvious from the tables, ethylene glycol diacetate (EGDA) in concentrations 25-55% (in water) can serve as binding solution or emulsion upon mixing with one volume chaotropic sample lysate to isolate RNA.

FIG. 1 shows a gel image of a denaturing gel analysis of the RNA samples as purified according to Example 4. The RNA of lanes 1-4 was isolated using a mix of 40% EGDA and 60% 5M GITC as RNA binding solution, from which was added 350 µL to 350 µL RNA containing cell lysate (cells lysed in 5 M GITC), resulting in a final concentration of 20% EGDA and 4 M GITC in water during binding of the RNA to the solid support. The RNA of lanes 5-8 was isolated by adding 70% ethanol/30% water in a 1:1 volume to the lysis buffer.

Example 4

A number of $10^6$ HeLa cells were contacted and lysed with 350 µL of 5 M guanidinium thiocyanate (GITC) solution. The lysate was passed over a spin column containing a porous polyethylene frit (NucleoSpin Filter) in order to obtain a cleared lysate. The flow-through was mixed with 350 µL of one of the following solutions: A) mixture of EGDA and 5 M GITC in a ratio of 40:60 and B) mixture of ethanol and water in a ratio 70:30. The resulting mixtures were passed over a silica containing spin column (NucleoSpin RNA Column) and further processes according to example 1. The RNA yield was determined spectrophotometrically. Contaminating DNA in the RNA eluate was determined by qPCR.

The different experimental approaches together with the quantity of the purified RNA and the degree of DNA contamination are summarized in Table 8:

TABLE 8

| | A 40% EGDA 60% 5M GITC | | B 70% ethanol 30% water | |
|---|---|---|---|---|
| prep # | DNA contamination [ng] | RNA yield [ng] | DNA contamination [ng] | RNA yield [ng] |
| 1 | 0.9 | 13680 | 10.2 | 18280 |
| 2 | 1.2 | 13400 | 1.2 | 18720 |
| 3 | 1.1 | 13400 | 12.7 | 17880 |
| 4 | 1.4 | 13880 | 5.8 | 18520 |
| average nucleic acid yield [ng] | 1.2 | 13590 | 7.5 | 18350 |

As obvious from the table the use of EGDA as binding solution results in RNA yields similar to those obtained with 70% ethanol as organic solvent.

The RNA was further analysed by denaturing gel electrophoresis in order to assess the RNA quality, see FIG. 1.

Example 5

RNA was isolated from a range of nine different RNA containing sample materials with varying sample amounts:
1. Mouse brain 20 mg
2. Corn leaves 100 mg
3. Wheat leaves 100 mg
4. Mouse kidney 10 mg
5. Mouse liver 10 mg
6. Mouse spleen 10 mg
7. Rat kidney 10 mg
8. Rat liver 10 mg
9. HeLa cells $10^6$ cells Sample material was lysed in 350 µL of 4 M GITC solution, passed over a silica containing spin column (NucleoSpin Protein Removal Column), the flow through was mixed with 350 µL each of a binding solution A) 70% ethylene carbonate, 50 mM $MgCl_2$ in water or a binding solution B) of 40% ethylene glycol diacetate, 3 M GITC and 150 mM $MgCl_2$ in water. The resulting mixtures were passed over a silica containing spin column (NucleoSpin RNA column). A 95 µL DNase containing reaction mixture was added to the column and incubated for 15 minutes. Subsequently the column was washed with wash buffers according to the NucleoSpin RNA user manual (Macherey-Nagel Inc., Bethlehem, Pa., USA). As reference preparations, RNA was isolated from the sample materials with the NucleoSpin RNA kit according to the user manual, in which a 70% ethanol solution is used as binding solution. RNA yields were determined spectrophotometrically.

Tables 9 and 10 show the RNA yield obtained with binding solution A) and B) relative to RNA yields obtained by RNA isolation with NucleoSpin RNA kit according to the user manual:

As obvious from the tables, ethylene carbonate and ethylene glycol diacetate can serve as binding buffer instead of a 70% ethanol solution and RNA yields can be higher for certain samples.

Figure 2:
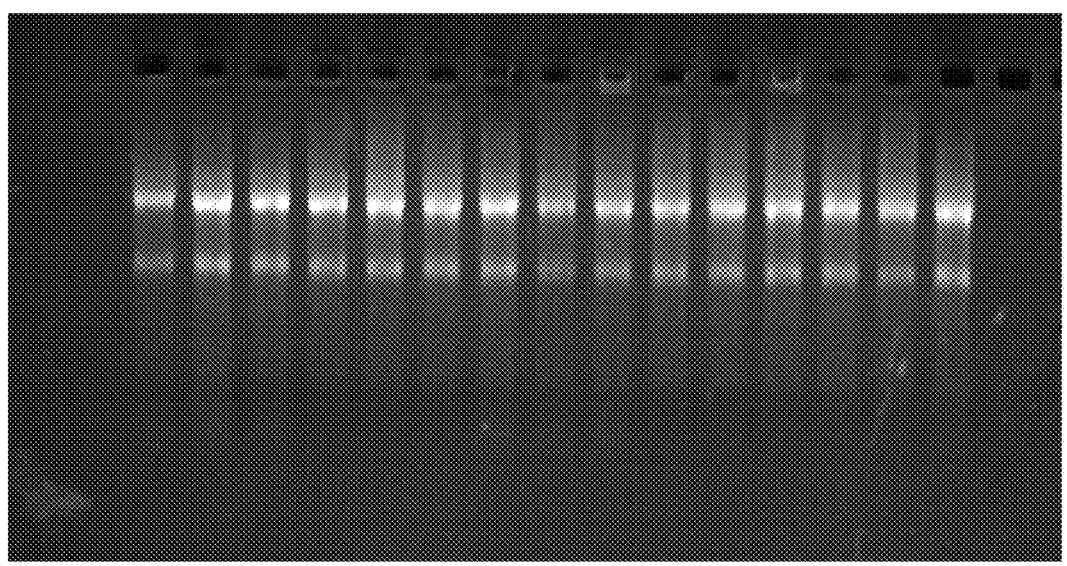
FIG. 2 shows a gel image of a denaturing gel analysis of the RNA samples as purified according to Example 6.

FIG. 2 shows a gel image of a denaturing gel analysis of the RNA samples as purified according to Example 6. The lanes contain the RNA samples as isolated by the following binding solutions:
Lane 1-3: Binding solution #1
Lane 4-6: Binding solution #2
Lane 7-9: Binding solution #5
Lane 10-12: Binding solution #6
Lane 13-15: Binding solution #9

Example 6

A number of $10^6$ HeLa cells were contacted and lysed with 350 µL of 4 M guanidinium thiocyanate (GITC) solution. The lysate is passed over a silica containing spin column (NucleoSpin Protein Removal Column) in order to obtain a cleared lysate. The flow-through was mixed with 350 µL of one of the following solutions. Subsequently, the mixture was passed over a silica containing spin column (NucleoSpin RNA column) and further processed according to the NucleoSpin RNA user manual.

Binding solution mixtures together with the obtained RNA yields are summarized in Table 11:

TABLE 11

| Binding Solution # | Binding solution | | RNA yield [µg] |
|---|---|---|---|
| | Substance A | Substance B | |
| 1 | Ethylene carbonate 80% | Water 20% | 17.8 |
| 2 | Ethylene carbonate 60% | Water 40% | 18.3 |
| 3 | Ethylene carbonate 40% | Water 60% | 0.6 |
| 4 | Ethylene carbonate 20% | Water 80% | 0.2 |
| 5 | Ethylene carbonate 80% | 5M GITC 20% | 17.1 |

TABLE 9

Binding Solution A: 70% ethylene carbonate, 50 mM MgCl2 in water

| prep # | Mouse brain | Corn leaves | Wheat leaves | Mouse kidney | Mouse liver | Mouse spleen | Rat kidney | Rat liver | HeLa cells |
|---|---|---|---|---|---|---|---|---|---|
| 1 | 106% | 71% | 77% | 335% | 6% | 190% | 18% | 9% | 94% |
| 2 | 127% | 62% | 60% | 296% | 2% | 234% | 17% | 12% | 137% |
| 3 | 93% | 63% | 56% | 337% | 6% | 211% | 23% | 10% | 102% |
| average | 109% | 66% | 64% | 323% | 5% | 212% | 19% | 10% | 111% |
| total average | | | | | 102% | | | | |

TABLE 10

Binding Solution B: 40% ethylene glycol diacetate, 3M GITC and 150 mM MgCl2 in water

| prep # | Mouse brain | Corn leaves | Wheat leaves | Mouse kidney | Mouse liver | Mouse spleen | Rat kidney | Rat liver | HeLa cells |
|---|---|---|---|---|---|---|---|---|---|
| 1 | 207% | 118% | 78% | 309% | 135% | 237% | 101% | 40% | 99% |
| 2 | 176% | 93% | 68% | 375% | 129% | 183% | 92% | 33% | 101% |
| 3 | 228% | 87% | 53% | 384% | 120% | 233% | 97% | 41% | 92% |
| average | 203% | 99% | 66% | 356% | 128% | 218% | 97% | 38% | 98% |
| total average | | | | | 145% | | | | |

TABLE 11-continued

| Binding Solution # | Binding solution Substance A | Substance B | RNA yield [µg] |
|---|---|---|---|
| 6 | Ethylene carbonate 60% | 5M GITC 40% | 18.4 |
| 7 | Ethylene carbonate 40% | 5M GITC 60% | 4.0 |
| 8 | Ethylene carbonate 20% | 5M GITC 80% | 2.1 |
| 9 | Ethnaol 70% | Water 30% | 18.3 |

As is obvious from the results, a solution containing 60-80% ethylene carbonate can be used as binding solution yielding an RNA amount similar to the control preparations, in which 70% ethanol was used as binding solution.

RNA isolated using binding solutions containing 60-80% ethylene carbonate were further analysed by gel electrophoresis shown in FIG. 2. As is obvious from the gel electrophoretic analysis, binding solutions containing 60-80% ethylene carbonate enable purification of RNA of high quality, indicated by the clear appearance of the 18S and 28S rRNA signals in the gel.

What is claimed is:

1. A buffer, comprising:
  a phenol-free RNA-binding buffer that allows RNA to bind selectively to an RNA-binding solid phase comprising:
  (a) at least one chaotropic agent; and
  (b) an organic solvent selected from the group consisting of ethylene carbonate or, ethylene glycol diacetate or a combination thereof.

2. The buffer of claim 1, wherein the at least one chaotropic agent is selected from the group consisting of guanidinium hydrochloride (GHCl), guanidinium thiocyanate, guanidinium isothiocyanate (GITC), sodium thiocyanate, sodium iodide, sodium perchlorate, sodium trichloracetate, sodium trifluoracetate, and urea.

3. The buffer of claim 1, wherein a concentration of the at least one chaotropic agent in the phenol-free RNA-binding buffer is from 0.5 M to 3 M.

4. The buffer according to claim 1, wherein a concentration of the organic solvent within the phenol-free RNA-binding buffer is between 10 percent v/v and 50 percent v/v.

5. The buffer according to claim 1, wherein the phenol-free RNA-binding buffer has a pH value of between 5.5 and 8.5.

6. A method for binding RNA selectively to an RNA-binding solid phase comprising:
  contacting an RNA-binding solid phase with an RNA-containing material provided in a phenol-free RNA-binding buffer that allows RNA to bind selectively to the RNA-binding solid phase comprising:
  at least one chaotropic agent; and
  an organic solvent selected from the group consisting of ethylene carbonate or, ethylene glycol diacetate or a combination thereof.

7. The method according to claim 6, wherein the RNA-binding solid phase is selected from a group consisting of silica, silica particles, silicon dioxide, diatomaceous earth, glass, alkylsilica, aluminum silicate, and borosilicate; nitrocellulose; diazotized paper; hydroxyl apatite; nylon; metal oxides; zirconia; alumina; polymeric supports, diethylaminoethyl- and triethylaminoethyl-derivatized supports, and hydrophobic chromatography resins.

8. A method for isolating purified RNA from a biological sample comprising the steps of:
  (a) generating a RNA-containing solution by lysing the biological sample with a phenol-free lysis solution comprising at least one chaotropic agent and optionally enhancing the lysis by mechanical, freeze-thawing-associated or enzymatic (pre-)treatment of the biological sample;
  (b) adding a solution comprising ethylene carbonate, ethylene glycol diacetate or a combination thereof to yield a RNA-binding solution that allows RNA to bind selectively to an RNA-binding solid phase;
  (c) contacting the RNA-binding solid phase with the RNA-binding solution of step (b) in order to bind the RNA to the RNA-binding solid phase, wherein the RNA-binding solid phase is selected from a group consisting of silica, silica particles, silicon dioxide, diatomaceous earth, glass, alkylsilica, aluminum silicate, and borosilicate; nitrocellulose; diazotized paper; hydroxyl apatite; nylon; metal oxides; zirconia; alumina; polymeric supports, diethylaminoethyl- and triethylaminoethyl-derivatized supports, and hydrophobic chromatography resins comprising one or more of:
    phenyl Sepharose;
    octyl Sepharose;
    silica; and
    silica containing spin column;
  (d) optionally performing a DNase digest and/or proteolytic digest;
  (e) optionally performing at least one washing step for washing RNA bound to the RNA-binding solid phase;
  (f) optionally eluting the bound RNA.

9. The method according to claim 8, wherein the phenol-free lysis solution further comprises at least one detergent and at least one chelating agent.

10. The method according to claim 8, wherein the biological sample is contacted between step (a) and step (b) to a DNA-binding solid support.

11. The method according to claims 8, wherein the organic solvent containing solution in step (b) is added to the RNA-containing solution of step (a) in a volume ratio of between 1:2 and 1:5.

12. A kit comprising:
  a. a phenol-free lysis solution;
  b. a solution comprising ethylene carbonate or, ethylene glycol diacetate or a combination thereof.

13. The kit according claim 12 further comprising one or more of the following:
  (a) one or more wash buffers;
  (b) a DNAse containing solution;
  (c) silica spin columns for DNA binding;
  (d) silica spin columns for RNA binding;
  (e) Tris-EDTA buffer or RNase-free H2O as elution buffer.

14. The buffer of claim 2, wherein the at least one chaotropic agent is guanidinium hydrochloride (GHCl) or guanidinium thiocyanate.

15. The buffer of claim 3, wherein a concentration of the at least one chaotropic agent in the RNA-binding buffer is between 0.75 M to 2.5 M.

16. The buffer of claim 3, wherein a concentration of the at least one chaotropic agent in the RNA-binding buffer is at least 1 M.

17. The buffer according to claim 4, wherein a concentration of the organic solvent within the RNA-binding buffer is between 15 percent v/v and 35 percent v/v.

18. The buffer according to claim 4, wherein a concentration of the organic solvent within the RNA-binding buffer is between 18 percent v/v and 25 percent v/v.

19. The buffer according to claim 5, wherein the phenol-free RNA-binding buffer has a pH value of between 6.0 and 8.0.

20. The buffer according to claim 5, wherein the phenol-free RNA-binding buffer has a pH value of between 6.5 and 7.5.

21. The method according claim 7, wherein the RNA-binding solid phase is silica.

22. The method according claim 7, wherein the RNA-binding solid phase is a silica containing spin column.

23. The method according to claim 10, wherein the biological sample is contacted between step (a) and step (b) to silica material as a DNA-binding solid support.

24. The method according to claim 10, wherein the biological sample is contacted between step (a) and step (b) to a silica containing spin column as a DNA-binding solid support.

25. The method according to claim 11, wherein the organic solvent containing solution in step (b) is added to the RNA-containing solution of step (a) in a volume ratio of between 1:3 and 1:4.

26. The method according to claim 11, wherein the organic solvent containing solution in step (b) is added to the RNA-containing solution of step (a) in a volume ratio of 1:3.5.

* * * * *